US00PP13962P39

(12) United States Plant Patent
Zerr

(10) Patent No.: US PP13,962 P3
(45) Date of Patent: Jul. 8, 2003

(54) POINSETTIA PLANT NAMED 'KAMP BURGUNDY'

(75) Inventor: Katharina Zerr, Hohr-Grenzhausen (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/108,480

(22) Filed: Mar. 29, 2002

(65) Prior Publication Data

US 2002/0157157 P1 Oct. 24, 2002

(30) Foreign Application Priority Data

Apr. 23, 2001 (EP) ..... 2001/0724

(51) Int. Cl.[7] ..... A01H 5/00

(52) U.S. Cl. ..... Plt./307

(58) Field of Search ..... Plt./303, 307

*Primary Examiner*—Bruce R. Campell
*Assistant Examiner*—June Hwu
(74) *Attorney, Agent, or Firm*—Foley & Lardner

(57) ABSTRACT

A new and distinct poinsettia plant named 'Kamp Burgundy' characterized by uniform, red-purple bract color; relatively compact, star-shaped, flat inflorescence; intense dark-green foliage with weak lobes; moderately compact, rounded plant habit; and medium to moderately late flowering response.

1 Drawing Sheet

Latin name of the genus and species of the plant claimed: *Euphorbia pulcherrima.*

Variety denomination: 'Kamp Burgundy'.

BACKGROUND OF THE INVENTION

The present invention relates to a new and distinct cultivar of poinsettia plant known by the cultivar name 'Kamp Burgundy', and botanically known as *Euphorbia pulcherrima.*

'Kamp Burgundy' derived from a naturally occurring mutation of the variety 'Fiscor' (U.S. Plant Pat. No. 9,364). 'Fiscor' is characterized by red colored bracts, dark-green foliage, and moderately compact, and rounded plant habit.

The mutation was discovered by Katharina Zerr, the inventor, in a greenhouse in Hillscheid, Germany, in December 1998. Among a group of flowering plants a darker flowered one with purple colored bracts was found, which appeared to be completely mutated. The plant was left to develop vegetative shoots, which were cut by the inventor and used for propagation (first asexual reproduction) in the spring of 1999. The resulting plants appeared uniform, and the purple bract color was stable. This result was confirmed when the propagation and examination was repeated on a larger scale in the fall of 2000.

Horticultural examination of the plant starting in 2000 and continuing thereafter has demonstrated that the combination of characteristics as herein disclosed for 'Kamp Burgundy' are firmly fixed and retained through successive generations of asexual reproduction.

BRIEF SUMMARY OF THE INVENTION

The following traits have been repeatedly observed and are determined to be basic characteristics of 'Kamp Burgundy', which in combination distinguish this Poinsettia as a new and distinct cultivar:

1. uniform, red-purple bract color;
2. relatively compact, star-shaped, flat inflorescence;

3. intense dark-green foliage with weak lobes;
4. moderately compact, rounded plant habit; and
5. medium to moderately late flowering response.

'Kamp Burgundy' has not been observed under all possible environmental conditions. The phenotype may vary significantly with variations in environment such as temperature, light intensity, and day-length. The following observations, measurements and comparisons describe plants grown in Hillscheid, Germany, under greenhouse conditions which approximate those generally used in commercial practice.

Of the may commercial cultivars known to the inventor, the most similar in comparison to 'Kamp Burgundy' are the parent cultivar 'Fiscor', the related cultivar 'Fiscor Dark-Red' (U.S. Plant Pat. No. 12,723), and the commercial cultivar 'Purple Reign' (unpatented).

In contrast to the red flowering cultivar 'Fiscor', 'Kamp Burgundy' has darker, purple colored bracts, somewhat smaller bracts and a slightly smaller plant habit. Due to its smaller bracts, 'Kamp Burgundy' is marketable about 7 days later than 'Fiscor'.

In comparison to 'Fiscor Dark Red', 'Kamp Burgundy' has a distinctly darker tone of bract color, somewhat smaller bracts, but plant habit is of approximately equal size.

In comparison to 'Purple Reign', 'Kamp Burgundy' has a more reddish and more intense, hue of bract color, while 'Purple Reign' has a more bluish hue and a stronger tendency to fading. Furthermore, 'Kamp Burgundy' has darker green foliage, and its plant habit is distinctly more compact than that of 'Purple Reign'.

BRIEF DESCRIPTION OF THE DRAWING

The accompanying color photographic drawing shows typical inflorescence and foliage of 'Kamp Burgundy', with colors being as true as possible with an illustration of this type. The photograph shows a mature potted plant.

DETAILED BOTANICAL DESCRIPTION

The plants described were grown in a greenhouse in Langley, British Columbia, Canada, in the fall of 2001. Rooted cuttings were planted into 6 inch pots on July 18, and were pinched on August 13, leaving 7 leaves. Initially, the temperature was between minimum 22° C. and 24.5° C. maximum (ventilation temperature) and from September to late October between 18° and 21° C., and 15° to 17° C. in November. The plants initiated flowers under short-day conditions after applying shading (black-out) from September 10 to the end of September. Observations and measurements were mainly taken around November 18, when the plants were 17.5 weeks old and when most varieties had begun flowering. In the following description color references are made to The Royal Horticultural Society Colour Chart (R.H.S.). The color values were determined indoors in a north light.

Classification:

*Botanical.*—*Euphorbia pulcherrima.*

*Commercial.*—Poinsettia cv. Kamp Burgundy.

Parentage: Naturally-occurring mutation of cultivar 'Fiscor'.

Plant:

*Form.*—Shrub, self-branching.

*Growth habit.*—Moderately compact, weak to medium growth, pinched plants are bushy and rounded in shape.

*Height* (*above soil line*).—34.1 cm.

*Width.*—55.1 cm.

*Average number of branches.*—6.1.

*Average number of inflorescence.*—5.8.

*Stem color.*—Ground color light green, RHS 144 B, most internodes reddish infused, the resulting color is near RHS 184 B.

*Rooting.*—Medium, sufficiently rooted for transplanting after about 20–24 days in a greenhouse at a temperature of 22–24° C.

*Blooming habit.*—Begin under natural short day conditions in fall; botanically (cyathia open) in early December; commercially (bracts colored, marketable) in early December.

*Flowering response time.*—About 10 weeks.

Foliage:

*Shape.*—Ovate with rounded base, weak lobes and acuminated tip.

*Margin.*—Entire.

*Texture.*—Upper surface: smooth and flat, only weakly veined, color of veins mainly light green, RHS 139 D, near the base RHS 184 A.

*Lower surface.*—Flat and smooth, except for the slightly protruding midrib and finer side veins in a pinnate pattern, the vein color is light pink, RHS 51 C, near the base, to whitish green, RHS 139 D, towards the tip.

*Size.*—Leaf blade length: 12.2 cm. Width: 8.3 cm.

*Petiole.*—Length: 6.5 cm on average.

*Quantity.*—About 45 leaves per plant.

*Color.*—Generally dark green, uniform. Mature foliage: upper surface, RHS 139 A. under surface, RHS 138 A. New foliage: upper side RHS 143 A. under side RHS 137 D. Leaf petiole: upper side deep purple, RHS 185 A. lower side dull purple-brown, RHS 184 B.

*Aspect.*—Petioles are horizontally directed, the leaf blades show slightly downward.

Disease resistance: No special observations made.

Flowering description: Whole inflorescence with surrounding bracts: just under medium sized, star-shaped, with the bracts horizontally or slightly upward directed, the bracts are arranged in a spiral around the axis with the size diminishing towards the tip.

*Diameter.*—About 26–27 cm.

*Number of bracts* (*size over 2 cm*) *per inflorescence.*—9–12.

*Keeping quality.*—Good quality will be maintained for about 4 weeks, no dropping of bracts, slight fading of the color may finally occur: to RHS 53 C or 53 D.

*Bracts.*—Shape: Ovate, with rounded bases, very weak to weak lobes, and acuminate tips. Size of the largest fully colored bract: 14.3 cm long, 9.0 cm wide. Texture: Smooth and flat, with the veins hardly visible, initially no rugosity, as the bracts mature the bracts may appear somewhat rippled, though comparatively little. Vein color: Upper side corresponds closely to bract color, lower side is dull pink, near RHS 51 B. Color: Generally intense red-purple, uniform. Upper surface: RHS between 53 A and 53 B. Lower surface: RHS 53 B. Petiole: 10–15 mm long, color: upper side RHS 60 A, lower side 51 B.

*Cyme.*—5–10 cyathia borne in a tight cluster, 20–22 in diameter.

*Cyathium.*—Ovate, about 6 mm in diameter, medium to light green colored, RHS 143 B.

*Peduncle.*—Light green, RHS 144 B, about 4 mm long.

*Nectar cups.*—Usually one per cyathium, about 5 mm wide, golden yellow colored, RHS 15 A to 23 A, near margin reddish infused: RHS 40 A.

Reproductive organs:

*Stamens.*—About 20–25 per cyathium, red filaments, between RHS 46 A and 46 B; moderate pollen, yellow, RHS 12 A.

*Pistil.*—1 per cyathium, style and stigma dark red, RHS 46 A, stigma trifurcate, 6-lobed.

*Ovaries.*—Light to medium green, RHS 143 B, initially obovate, later triangular, diameter 4 mm, 6 mm long, 3 ovules.

*Fruit/seed set.*—No observation to date.

I claim:

1. A new and distinct cultivar of Poinsettia plant named 'Kamp Burgundy', as illustrated and described herein.

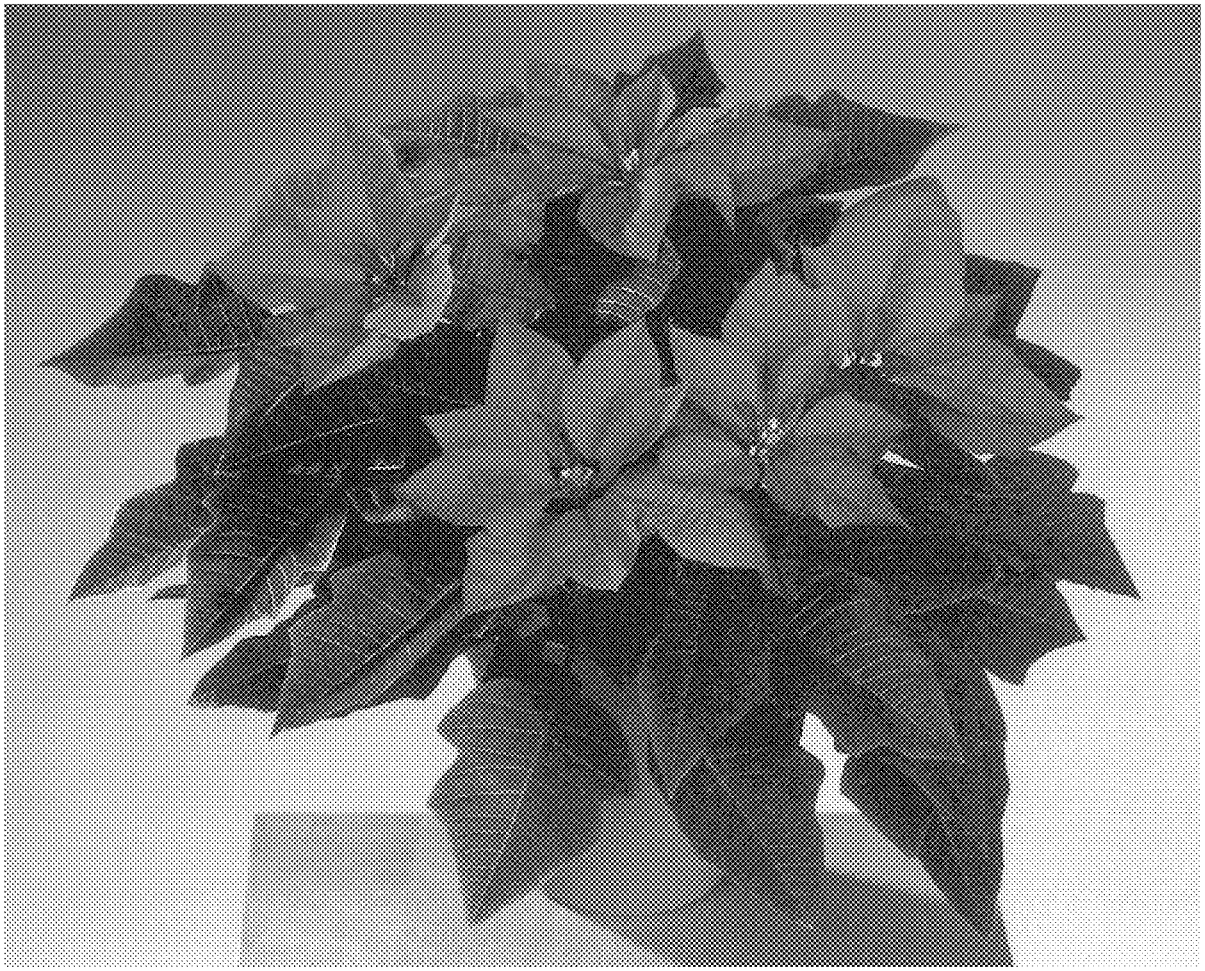

* * * * *